United States Patent
Moon et al.

(10) Patent No.: US 10,261,100 B2
(45) Date of Patent: Apr. 16, 2019

(54) HIGH SPEED ON-LINE LIPID EXTRACTION DEVICE, SYSTEM AND METHOD FOR EXTRACTING AND ANALYZING LIPID FROM BIOLOGICAL SAMPLE USING THE DEVICE

(71) Applicant: University-Industry Foundation, Yonsei University, Seoul (KR)

(72) Inventors: Myeong Hee Moon, Gyeonggi-do (KR); Ju Yong Lee, Seoul (KR)

(73) Assignee: University-Industry Foundation, Yonsei University, Seoul (KR)

( * ) Notice: Subject to any disclaimer, the term of this patent is extended or adjusted under 35 U.S.C. 154(b) by 157 days.

(21) Appl. No.: 15/352,653

(22) Filed: Nov. 16, 2016

(65) Prior Publication Data

US 2017/0176471 A1    Jun. 22, 2017

(30) Foreign Application Priority Data

Dec. 22, 2015 (KR) .................... 10-2015-0183438

(51) Int. Cl.
| | |
|---|---|
| *B01D 15/30* | (2006.01) |
| *G01N 33/92* | (2006.01) |
| *B01J 20/281* | (2006.01) |
| *G01N 33/50* | (2006.01) |
| *G01N 30/90* | (2006.01) |
| *B01D 15/00* | (2006.01) |
| *G01N 1/40* | (2006.01) |
| *G01N 30/20* | (2006.01) |
| *G01N 30/72* | (2006.01) |
| *G01N 30/88* | (2006.01) |

(52) U.S. Cl.
CPC .......... *G01N 33/92* (2013.01); *B01D 15/305* (2013.01); *G01N 30/482* (2013.01); *G01N 1/405* (2013.01); *G01N 30/20* (2013.01); *G01N 30/7233* (2013.01); *G01N 2030/8813* (2013.01); *G01N 2560/00* (2013.01)

(58) Field of Classification Search
CPC ........ G01N 33/92; G01N 33/50; G01N 33/48; G01N 30/90; G01N 30/482; G01N 30/48; G01N 30/02; B01D 15/305; B01D 15/30; B01D 15/26; B01D 15/08; B01D 15/00
USPC .......................... 436/71; 422/400, 101, 50
See application file for complete search history.

(56) References Cited

U.S. PATENT DOCUMENTS

| | | | |
|---|---|---|---|
| 6,321,609 B1 * | 11/2001 | Mengel ............... | G01N 1/2273 73/863.21 |
| 8,211,308 B2 | 7/2012 | Kale | |
| 8,273,248 B1 | 9/2012 | Kale | |
| 8,383,845 B2 | 2/2013 | Catchpole et al. | |
| 2007/0036685 A1 * | 2/2007 | Bakry ................. | B01J 20/3242 422/400 |
| 2008/0264792 A1 * | 10/2008 | Moon ................... | B01D 63/02 204/452 |

OTHER PUBLICATIONS

Lee et al, On-line high speed lipid extraction for nanoflow liquid chromatography-tandem mass spectrometry, Journal of Chromatogrphy A, 2016, 1464, 12-20. (Year: 2016).*

* cited by examiner

*Primary Examiner* — Christine T Mui
(74) *Attorney, Agent, or Firm* — Hammer & Associates, P.C.

(57) ABSTRACT

The present invention provides a lipid extraction device comprising a capillary tube, wherein the capillary tube comprises a first region containing a first filler; and a second region present in a region other than the first region and containing a second filler having polarity different from the first filler. The present invention also provides a system and a method for extracting and analyzing lipids from a biological sample using the lipid extraction device.

16 Claims, 3 Drawing Sheets

1. 14:0-LPG
2. 14:0-LPE
3. 18:0-LPG
4. 12:0/12:0-PG
5. 12:0/12:0-PE
6. 15:0/15:0-PG
7. 16:0/18:2-PI
8. 16:0/16:0-PG
9. d18:1/16:0-SM
10. 18:0/18:0-PS

[Figure 4]

| m/z | Species | Folch | | Modified Folch & MeOH | | QuEChERS | on-line Extraction |
|---|---|---|---|---|---|---|---|
| | | SpeedVac | under $N_2$ | SpeedVac | under $N_2$ | | |
| 424.3 | 14:0-LPE | 72.9±6.5 | 77.4±7.2 | 94.6±13.5 | 94.4±14.2 | 78.7±9.2 | 90.2±7.9 |
| 480.4 | 18:0-LPE | 76.5±9.4 | 76.8±11.8 | 89.3±11.4 | 95.0±12.3 | 90.3±13.9 | 86.3±12.1 |
| 578.4 | 12:0/12:0-PE | 84.3±9.8 | 82.8±14.3 | 91.8±15.0 | 97.3±11.5 | 98.9±14.4 | 91.8±15.0 |
| 634.5 | 14:0/14:0-PE | 88.9±7.2 | 96.3±9.7 | 97.5±15.8 | 92.8±7.6 | 94.5±13.3 | 103.1±10.8 |
| 455.3 | 14:0-LPG | 72.4±8.2 | 69.1±8.7 | 100.3±10.5 | 97.3±9.8 | 92.5±9.1 | 89.6±15.8 |
| 511.3 | 18:0-LPG | 77.7±10.6 | 76.2±8.0 | 101.6±8.3 | 97.8±9.0 | 98.8±13.4 | 97.4±10.2 |
| 609.4 | 12:0/12:0-PG | 82.3±5.1 | 85.4±4.6 | 91.8±4.5 | 95.7±6.1 | 90.2±10.9 | 90.1±8.3 |
| 693.5 | 15:0/15:0-PG | 89.2±5.9 | 91.2±6.4 | 91.2±7.7 | 95.6±7.6 | 91.7±8.3 | 95.6±9.7 |
| 496.4 | 16:0-LPC | 70.9±9.2 | 71.5±8.5 | 91.5±8.5 | 91.1±7.2 | 85.5±6.8 | 86.9±7.5 |
| 734.5 | 16:0/16:0-PC | 83.9±8.6 | 80.2±8.4 | 89.4±9.0 | 88.6±12.0 | 91.6±11.5 | 89.3±12.7 |
| 846.6 | 20:0/20:0-PC | 92.7±9.9 | 94.4±6.0 | 97.9±8.7 | 96.0±7.9 | 89.1±8.1 | 93.0±9.2 |
| 678.5 | 14:0/14:0-PS | 84.9±10.5 | 81.0±9.6 | 92.2±11.9 | 94.5±14.0 | 95.2±13.9 | 94.5±13.6 |
| 790.6 | 18:0/18:0-PS | 84.2±10.2 | 88.1±11.4 | 90.8±12.1 | 90.1±13.1 | 90.2±12.8 | 88.8±11.2 |
| 833.6 | 16:0/18:2-PI | 90.5±2.5 | 90.2±5.9 | 92.0±6.5 | 90.7±8.1 | 93.0±7.8 | 92.8±4.2 |
| 693.5 | d18:0/12:0-SM | 89.1±6.5 | 87.8±6.3 | 95.6±10.3 | 94.6±14.1 | 96.6±7.6 | 89.9±9.9 |
| 747.5 | d18:1/16:0-SM | 85.7±5.6 | 88.6±5.5 | 90.6±8.3 | 93.4±7.0 | 93.1±8.8 | 89.8±9.1 |
| 644.5 | MHC | 73.2±8.5 | 78.4±8.0 | 97.1±16.1 | 95.6±8.3 | 100.0±8.8 | 94.9±8.3 |

Figure 5

[Formula 1]

HIGH SPEED ON-LINE LIPID EXTRACTION DEVICE, SYSTEM AND METHOD FOR EXTRACTING AND ANALYZING LIPID FROM BIOLOGICAL SAMPLE USING THE DEVICE

TECHNICAL FIELD

The present invention relates to a high speed online lipid extraction device connectable to a liquid chromatography-mass spectrometer, and specifically relates to an online lipid extraction device which may perform rapid lipid extraction and at the same time qualitative and quantitative analyses when a urinary or plasma sample is directly injected to the developed online lipid extraction device. The present invention also relates to a system and a method for extracting and analyzing lipids from a biological sample using the developed online lipid extraction device.

BACKGROUND ART

Lipids are called the three major nutrients necessarily required in a biological body, together with proteins and carbohydrates, and their main role is known as the energy storage and in vivo various cell membrane components. In addition, hundreds of hormones present in the biological body also fall in a field of lipids, and it is known that the lipid plays a very important role as a signaling material, such as activation of genes in response to a variety of lipids in nuclear receptors of cells being the basic structural units of the body.

Since lipids have mostly complex lipid characteristics due to amphoteric properties and it takes a long time in the case of the liquid-liquid extraction method, the demand for new technique which can simply extract only lipids from the biological sample is continuously growing.

The Folch method is widely used in the biological and biochemical field to date as a first way in 1956 which can extract lipids from a biological sample using the organic solvents of methanol and chloroform and distilled water. This method is based on the liquid-liquid extraction method, and has been used while changing some of kinds and composition in the organic solvents so as to be suitable to the kind of lipids to be analyzed.

The inventors attempted to develop a simple extraction method by applying to the lipid extraction the QuEChERS method widely used in food analysis and environmental analysis fields. This extraction method succeeded in significantly reducing the extraction time to about 10 minutes, while having also excellent extraction efficiency, compared to the widely used liquid-liquid extraction method. However, this method has a disadvantage that it cannot be connected online to the chromatography-mass spectrometer due to non-resuable magnesium sulfate for absorbing moisture, and the process of absorbing moisture is an exothermic process, so that the risk that can result in modification of the lipid exists.

Upon reviewing patent references, it can be seen that most references are based on the liquid-liquid extraction method and take the expanded form (U.S. Pat. No. 8,383,845 B2; U.S. Pat. No. 8,273,248 B1; U.S. Pat. No. 8,211,308 B2).

DISCLOSURE

Technical Problem

It is the object of the present invention to provide an online lipid extraction device which may perform rapid lipid extraction and at the same time qualitative and quantitative analyses, and a system and a method for extracting and analyzing lipids from a biological sample using the same.

Technical Solution

To achieve the above mentioned object, the present invention provides a lipid extraction device comprising a capillary tube, wherein the capillary tube comprises a first region containing a first filler; and a second region present in a region other than the first region and containing a second filler having polarity different from the first filler.

The lipid extraction device according to the present invention may further comprise a filter that is installed on both ends of the capillary tube.

The first filler in the present invention may be hydrophilic interaction liquid chromatography beads (HILIC).

The second filler in the present invention may be at least one selected from the group consisting of C4 beads containing butyl chains, C8 beads containing octyl chains, and C18 beads containing octadecyl chains.

The lipid extraction device according to the present invention may further comprise a porous plate installed on both ends of the capillary tube and comprising pores having an average size of 0.1 to 1.5 μm.

In addition, the present invention provides a system for extracting and analyzing lipids comprising a sample injector; a first valve connected with the sample injector via a first capillary tube; a first joint connected with the first valve via a second capillary tube; the above mentioned lipid extracting device having the inlet side connected with the first joint via a third capillary tube and the outlet side connected with the first valve via a fourth capillary tube; a second joint connected with the first valve via a fifth capillary tube; an analytical column connected with the second joint via a sixth capillary tube; a mass spectrometer connected with the analytical column; and a second valve connected with the second joint via a seventh capillary tube, connected with a eighth capillary tube, connected with the first joint via a ninth capillary tube and connected with a tenth capillary tube.

The sample injector in the present invention is an autosampler, which may be mounted on high-performance liquid chromatography (HPLC).

The first valve in the present invention is a six port valve comprising a first port to a sixth port, which is mounted on the high-performance liquid chromatography (HPLC), and the first port of the first valve may be connected with the first capillary tube, the second port of the first valve connected with the second capillary tube, the third port of the first valve connected with the fourth capillary tube, and the fourth port of the first valve connected with the fifth capillary tube.

The second valve in the present invention is the six port valve comprising the first port to the sixth port, which is mounted on the mass spectrometer, and the first port of the second valve may be connected with the seventh capillary tube, the second port of the second valve connected with the eighth capillary tube, the third port of the second valve connected with the ninth capillary tube, and the fourth port of the second valve connected with the tenth capillary tube.

The inner diameter of the first capillary tube to the ninth capillary tube in the present invention may be 50 to 100 μm, and the inner diameter of the tenth capillary tube may be 5 to 40 μm.

The first joint in the present invention is a T joint, and the second joint is a cross joint, wherein a wire connected with an electrode of the mass spectrometer may be installed on the second joint.

The analytical column in the present invention comprises C18 beads containing octadecyl chains, which may have a taper structure at the end.

In addition, the present invention provides a method for extracting and analyzing lipids which uses the above mentioned system for extracting and analyzing lipids, and comprises a sample injection step, an internal standard injection step and a separation step.

In the sample injection step according to the present invention, a fluid may be introduced through the sample injector and then moved into the eighth capillary tube, via the first capillary tube, the first port and the second port of the first valve, the second capillary tube, the first joint, the third capillary tube, the lipid extraction device, the fourth capillary tube, the third port and the fourth port of the first valve, the fifth capillary tube, the second joint, the seventh capillary tube, and the first port and the second port of the second valve.

In the internal standard injection step according to the present invention, a fluid may be introduced through the sample injector and then moved into the analytical column, via the first capillary tube, the first port and the fourth port of the first valve, the fifth capillary tube, the second joint, and the sixth capillary tube.

In the separation step according to the present invention, a fluid may be introduced through the sample injector and then moved into the first joint via the first capillary tube, the first port and the second port of the first valve and the second capillary tube, and some of the fluid in the first joint may be moved into the analytical column via the third capillary tube, the lipid extraction device, the fourth capillary tube, the third port and the fourth port of the first valve, the fifth capillary tube, the second joint and the sixth capillary tube, and the remaining fluid in the first joint may be moved into the tenth capillary tube via the ninth capillary tube, and the third port and the fourth port of the second valve.

Effects of Invention

According to the invention, the rapid lipid extraction and at the same time the qualitative and quantitative analyses may be carried out, the qualitative and quantitative analyses of lipids in just a small volume of the liquid biological samples may be carried out, the modification of the samples may be inhibited, since the samples are not exposed to air, and simultaneous extraction of various kinds of lipid samples is also possible within a short time, since the extraction process is very simple.

DETAILED DESCRIPTION FOR CARRYING OUT INVENTION

Hereinafter, the present invention is explained in detail.

1. Lipid Extraction Device

Figure 1:
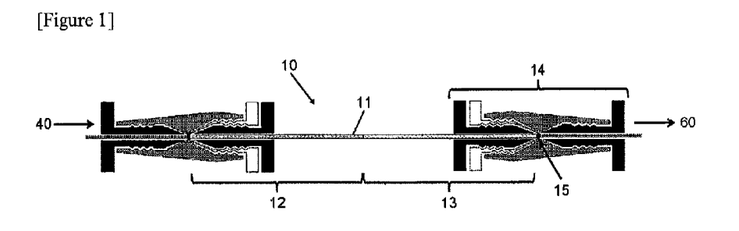
FIG. 1 is a cross-sectional view of the lipid extraction device according to the present invention.

FIG. 1 is a cross-sectional view of the lipid extraction device according to the present invention, and the lipid extraction device (10) of the present invention can be equipped with the capillary tube (11), the first filler (12), the second filler (13), the filter (14), the porous plate (15), and the like.

The capillary tube (11) serves to accommodate the filler for extracting lipids therein, which may be an elongated tube. The material of the capillary tube (11) is not particularly limited, but may be, for example, fused silica, natural quartz, doped fused silica, etc., in which the capillary tube may be coated with polyimide or the like. The size of the capillary tube (11) is not particularly limited, and for example, the length may be 1 to 10 cm, the outer diameter 250 to 500 μm, and the inner diameter 20 to 200 μm.

Figure 5:
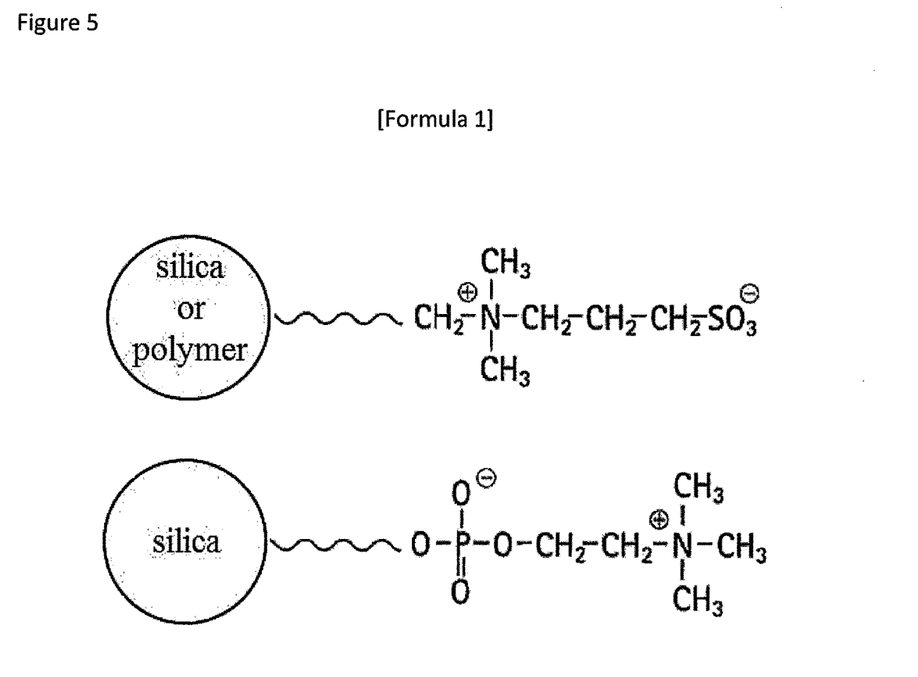
FIG. 5 shows an example of the HILIC bead, formula (1).

The first filler (12) serves to mainly adsorb lipids having strong polarity such as lysophospholipids or oxidized phospholipids as a stationary phase. The first filler (12) may be polar or hydrophilic filler. The first filler (12) may be filled in one side of the capillary tube (11), for example in the inlet side of the capillary tube (11). The average size of the first filler (12) is not particularly limited and may be, for example, 2 to 10 μm, preferably 3 to 5 μm, in accordance with the performance of high performance liquid chromatography. An amount of filling the first filler (12) is not particularly limited and may be, for example, 0.5 to 5 cm, preferably 1 to 3 cm based on the length of the capillary tube (11). Kinds of the first filler (12) are not particularly limited and may be, for example, hydrophilic interaction liquid chromatography beads (HILIC beads). The HILIC beads may be those that anions, cations or zwitterions are bound on porous silica or polymer particles directly or indirectly via a linker or the like. As a polymer, polymethyl methacrylate (PMMA), polystyrene-divinylbenzene (PS-DVB), polyethylene glycol, dextran and the like can be used. As zwitterions, sulfobetaine ions, phosphorylcholine ions, ammoniumsulfonic acid ligands and the like can be used. One example of the HILIC bead is as formula (1), see FIG. 5.

The second filler (13) serves to adsorb other lipids except for polar lipids as stationary phase. The second filler (13) may have polarity different from the first filler (12), and may be, for example, non-polar or hydrophobic filler. The second filler (13) may be filled in one side of the capillary tube (11), for example in the outlet side of the capillary tube (11). The average size of the second filler (13) is not particularly limited, and may be, for example, 2 to 10 μm, preferably 3 to 5 μm in accordance with the performance of high performance liquid chromatography. An amount of filling the second filler (13) is not particularly limited, and may be, for example, 0.5 to 5 cm, preferably 1 to 3 cm, based on the length of the capillary tube (11). Kinds of the second filler (13) are not particularly limited, and may be, for example, at least one selected from C4 beads, C8 beads, and C18 beads. C4 beads, C8 beads, and C18 beads may be those that butyl, octyl, and octadecyl carbon chains are bound on porous silica or polymer particles directly or indirectly via a linker or the like, respectively. Preferably, the C4 beads may be used, which can reduce the width of a separation peak in a subsequent separation process.

The filter (14) serves to block escape of the filler (12, 13) filled in the capillary tube (11) by being installed on both ends of the capillary tube (11). As the filter (14), for example, an inline filter may be utilized.

The porous plate (15) serves to substantially prevent separation of the filler (12, 13) by being installed on both ends of the capillary tube. The porous plate (15) may be attached to the filter (14). The porous plate (15) has a number of pores, the average size of which must be less than the size of the filler (12, 13), and may be, for example, 0.1 to 1.5 μm.

The inlet side of the lipid extraction device (10) can be connected to the first valve (40) direction, and the outlet side can be connected to the analysis column (60) direction.

The method for manufacturing the lipid extraction device (10) is as follows. To charge the fillers (12, 13) in the capillary tube (11), after connecting the filter (14) only at one end of the capillary tube (11), the other end is immersed in the slurry made of the second filler (13) and a solvent and pushed by high-pressure gas to suck the filler up. The solvent may be, for example, a mixture of water and alcohol (methanol, etc.), and the mixing ratio may be 20 to 40% of water and 60 to 80% of alcohol by a volume ratio. Gas may be, for example, an inert gas (helium, etc.), and the gas pressure may be, for example, 500 to 1500 psi. After filling the second filler (13) by the capillary tube length of 0.5 to 5 cm, the first filler (12) is also filled as slurry made in the same way in the other side of the capillary tube (11) and the other end of the capillary tube (11) is also blocked by the filter (14).

Conventionally, there was no column type lipid extraction device that can be connected online to a mass spectrometer as in the present invention, whereas in the present invention, the column type lipid extraction device comprising the filler was first developed.

2. System for Extracting and Analyzing Lipids

Figure 2:
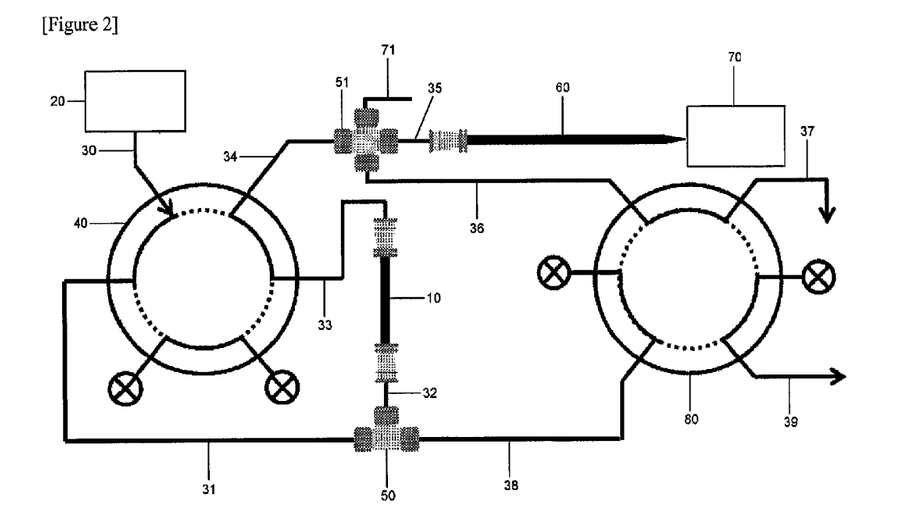
FIG. 2 is a configuration diagram of the system for extracting and analyzing lipids according to the present invention.

FIG. 2 is a configuration diagram of the system for extracting and analyzing lipids according to the present invention, and the system of the present invention can be equipped with the lipid extraction device (10), the sample injector (20), the first capillary tube (30), the second capillary tube (31), the third capillary tube (32), the fourth capillary tube (33), the fifth capillary tube (34), the sixth capillary tube (35), the seventh capillary tube (36), the eighth capillary tube (37), the ninth capillary tube (38), the tenth capillary tube (39), the first valve (40), the first joint (50), the second joint (51), the analytical column (60), the mass spectrometer (70), the wire (71), the second valve (80), and the like.

The sample injector (20) serves to inject the samples. The sample injector (20) may be, for example, an autosampler, which may be mounted on high performance liquid chromatography (HPLC). A pump may be connected before the sample injector (20).

The first capillary tube (30) serves to connect the sample injector (20) and the first port of the first valve (40), the second capillary tube (31) serves to connect the second port of the first valve (40) and the first joint (50), the third capillary tube (32) serves to connect the first joint (50) and the lipid extraction device (10), the fourth capillary tube (33) serves to connect the lipid extraction device (10) and the third port of the first valve (40), the fifth capillary tube (34) serves to connect the fourth port of the first valve (40) and the second joint (51), the sixth capillary tube (35) serves to connect the second joint (51) and the analytical column (60), the seventh capillary tube (36) serves to connect the second joint (51) and the first port of the second valve (80), the eighth capillary tube (37) serves to discharge the waste by being connected with the second port of the second valve (80), the ninth capillary tube (38) serves to connect the first joint (50) and the third port of the second valve (80), and the tenth capillary tube (39) serves to control the flow rate flowing towards the lipid extraction device (10) and the analytical column (60) by being connected with the fourth port of the second valve (80).

The inner diameter of the first capillary tube (30) to the ninth capillary tube (38) may be for example 50 to 100 μm. The inner diameter of the tenth capillary tube (39) must be less than the inner diameter of the first capillary tube (30) to the ninth capillary tube (38), and may be, for example, 5 to 40 μm. The tenth capillary tube (39) may be a pressure capillary tube (pressure capillary tube) for sending the sample and the solvent towards the analytical column (60), and control the flow rate flowing towards the lipid extraction device (10) and the analytical column (60) by controlling the length of the tenth capillary tube (39). Since pressure is much applied by utilizing the capillary tubes, it is preferred to use ultrahigh pressure LC (UPLC) that can endure 600 atm or more as LC, rather than HPLC that endures 400 atm.

The first valve (40) and the second valve (80) serve to change the flow path by being connected with the lipid extraction device (10), the sample injector (20), the analytical column (60), and the like. The online lipid extraction device (10) can be constructed via these two valves (40, 80) to be connectable to the liquid chromatography and the mass spectrometer (70). The first valve (40) and the second valve (80) may be equipped with a plurality of ports, and may be, for example, a six port valve. In FIG. 2, the first port of the first valve (40) may be located at the left top, the second port at the left center, the third port at the right center, the fourth port at the right top, the fifth port at the left bottom, and the sixth port at the right bottom. In FIG. 2, the first port of the second valve (80) may be located at the left top, the second port at the right top, the third port at the left bottom, the fourth port at the right bottom, the fifth port at the left center, and the sixth port at the right center. The fifth port and the sixth port of the first valve (40) and the second valve (80) are blocked, respectively. The first valve (40) may be mounted on the HPLC, and the second valve (80) may be mounted on the mass spectrometer (70).

The first joint (50) and the second joint (51) serve as the branch point for changing the flow path. The first joint (50) is comprised of, for example, a T joint, and may be each branched towards the lipid extraction device (10), the first valve (40), and the second valve (80). The second joint (51) is comprised of, for example, a cross joint, and may be each branched towards the first valve (40), the analytical column (60), and the second valve (80). The wire (71) may be installed on one side of the second joint (51), and an electrode of the mass spectrometer (70) may be connected through this wire (71).

The analytical column (60) serves to analyze lipids quantitatively and/or qualitatively, which can separate lipids trapped in the lipid extraction device (10) depending on polarity. The analytical column (60) may be a separately self-made column, and also mounted on the HPLC. The analytical column (60) may be a column that the filler is filled in the capillary tube as a stationary phase, similarly to the lipid extraction device (10). The material of the capillary tube may be, for example, fused silica, natural quartz, doped fused silica, etc., and the length of the capillary tube may be 5 to 30 cm, the outer diameter 250 to 500 μm, and the inner diameter 20 to 200 μm. As the filler used in the analytical column (60), the beads having higher non-polarity than the beads used in the online lipid extraction device, preferably C18 beads, can be freely used. The average size of the filler may be, for example, from 2 to 10 μm, and the amount of filling may be, for example, 5 to 30 cm, based on the length of the capillary tube. One end of the analytical column (60) may be blocked by the inline filter, and the like, so as not to leak the filler, and the other end of the analytical column (60) may have a taper structure as a needle, so as to well perform electrospray ionization towards the mass spectrometer (70). The length of the taper structure at the end may be, for example, 5 to 20 μm.

The mass spectrometer (70) serves to analyze lipids quantitatively and/or qualitatively, which can analyze the material ionized by vaporizing the sample, followed by ionization in an electrospray way, depending on the mass. The wire (71) may be installed on the second joint (51) for ionization. The wire (71) may be made of a metal such as platinum (Pt). Although FIG. 2 was illustrated to adjoin the analytical column (60) and the mass spectrometer (70), they are actually apart in a certain interval, whereby the sample and the like can be sprayed into the air towards the mass spectrometer (70).

3. Method for Extracting and Analyzing Lipids

The method for extracting and analyzing lipids according to the present invention uses the system for extracting and analyzing lipids, such as that in FIG. 2. The present method can be largely comprised of three steps, and specifically, a sample injection step, an internal standard injection step and a separation step. It is not restricted to change the order of the sample injection step and the internal standard injection step. In addition, the present method may include a sample pretreatment step before the sample injection step.

As a solvent in a mobile phase, two kinds of the first solvent and the second solvent may be used. The first solvent may be a hydrophilic solvent for injecting a sample into the lipid extraction device (10) and washing impurities such as ions, salts and hydrophilic peptides. The second solvent may be a hydrophobic solvent to separate and detect lipids by moving the lipids remained in the lipid extraction device (10) into the analytical column (60) and the mass spectrometer (70). The first solvent (solvent A) may be a polar solvent, which may comprise, for example, 80 to 100% of water and 0 to 20% of acetonitrile by a volume ratio. The second solvent (solvent B) may be an organic solvent, which may comprise, for example a mixture of 10 to 30% of acetonitrile, 0 to 30% of methanol and 40 to 70% of isopropanol by a volume ratio. To aid ionization on introducing the sample into the mass spectrometer, 1 to 10 mM of ammonium formate and 0.01 to 0.05% of ammonium hydroxide may be added to each solvent. The first solvent only may be used until the sample injection step and the internal standard injection step, and the gradient elution method of gradually changing the amount of the second solvent may be used in the separation step.

Table 1 shows valve settings in each step, which are settings to change flow paths. Referring to FIG. 2, in the six port valve (40, 80), A mode is indicated by a solid line, and B mode is indicated by a broken line, so that at least four flow path modes are permitted depending on a combination of the valve modes.

TABLE 1

|  | First Valve (40) | Second Valve (80) |
| --- | --- | --- |
| First Step: specimen sample injection | A | A |
| Second Step: internal standard injection | B | B |
| Third Step: separation | A | B |

— A, • • • B

First, only the first solvent may be used in the sample introduction step. In this step, the flow rate may be, for example, 0.1 to 3 μL/min. All the modes of the first valve (40) and the second valve (80) in the sample injection step are A mode, where the fluid is introduced from the sample injector (20) via the first capillary tube (30) into the first port of the first valve (40), and then reached via the second port of the first valve (40) and the second capillary tube (31) to the first joint (50). At this time, since the fifth port of the second valve (80) is blocked, the fluid does not flow towards the ninth capillary tube (38), but flows via the third capillary tube (32) towards only the lipid extraction device (10). Thereafter, the fluid reaches to the second joint (51), via the fourth capillary tube (33), the third port and the fourth port of the first valve (40) and the fifth capillary tube (34). In the second joint (51), the fluid does not flow towards the analytical column, but flows via the seventh capillary tube (36) towards the second valve (80), and then is discharged via the first port and the second port of the second valve (80) from the eighth capillary tube (37). This phenomenon occurs because the fluid does not flow towards the column in the conditions that the analytical column (60) is almost blocked by being filled with the C18 filler, while the seventh capillary tube (36) and the eighth capillary tube (37) are empty capillary tubes. Hydrophilic peptides, low-molecular materials, inorganic ions and the like may be removed by draining the first solvent for 1 to 20 minutes after the sample is adsorbed on the lipid extraction device (10).

Next, only the first solvent can be used in the internal standard injection step. In this step, the flow rate may be, for example, 0.1 to 3 μL/min. In the internal standard injection step, all the modes of the first valve (40) and the second valve (80) are B mode, where since the sections of the first port and the second port of the first valve (40) are blocked, the sections of the first port and the fourth port are connected and the sections of the fourth port and the third port are also blocked, the fluid is introduced from the sample injector (20) via the first capillary tube (30) into the first port of the first valve (40), and then does not flow towards the lipid extraction device (10), but flows via the fourth port of the first valve (40) and the fifth capillary tube (34) into only the second joint (51). In the second valve (80), since the sections of the first port and the second port are blocked and the fifth port is also blocked, the fluid does not flow towards the second valve (80), but flows, in the second joint (51), via the sixth capillary tube (35) into only the analytical column (60). At this time, the internal standard is injected to be adsorbed directly at the inlet of the analytical column (60). The internal standard cannot be affected by the sample injection step and the impurity removal step due to direct injection of the internal standard into the analytical column (60) other than the lipid extraction device (10).

Next, in the separation step, all of the first solvent and second solvent can be used. At this step, the flow rate must be greater than the previous steps, and may be at least 5 μL/min or more. The upper limit of the flow rate varies depending on the size of the tenth capillary tube (39), and may be, for example, 50 μL/min. In the separation step, the first valve (40) is A mode and the second valve (80) is B mode, where the fluid may flow into the analytical column (60), via the sample injector (20), the first capillary tube (30), the first port and the second port of the first valve (40), the second capillary tube (31), the first joint (50), the third capillary tube (32), the lipid extraction device (10), the fourth capillary tube (33), the third port and the fourth port of the first valve (40), the fifth capillary tube (34), the second joint (51), and the sixth capillary tube (35). In addition, the fluid in the first joint (50) may flow into the tenth capillary tube (39) via the ninth capillary tube (38), and the third port and the fourth port of the second valve (80). Since the sections of the first port and the second port of the second valve (80) are blocked and the fifth port is also blocked, the fluid in the second joint (51) does not flow towards the second valve (80).

Thus, in the first joint (50), the solvent is divided to move, that is, some of the solvent passes through the lipid extraction device (10) and the analytical column (60) in turn, and then flows to the inlet of the mass spectrometer (70), and the remaining solvent passes through the ninth capillary tube (38) and the second valve (80), and then flows into the tenth capillary tube (39). By adjusting the length of the tenth capillary tube (39), the flow rate of flowing from the first joint (50), which is a branch point, towards the lipid extraction device (10) may be 1 to 20% of the total flow rate, and the flow rate of flowing from the first joint (50) towards the second valve (80) may be 80 to 99% of the total flow rate. Although the flow rate of the fluid which flows out from the sample injector (20) may be a unit of from several to tens μL/min, the flow rate is controlled for the fluid to flow into a direction of the analytical column (60) and the mass spectrometer (70) by 300 to 1000 nL/min by adjusting the length of the tenth capillary tube (39), so that the solvent may be minimized on analyzing the mass to increase the ionization efficiency.

In the separation step the gradient elution method is used, that is, 100% of the first solvent has been used until the previous steps, and as the separation step starts, the ratio of the second solvent is gradually increased. For example, for 0.1 to 3 minutes from the beginning of the separation step the ratio of the second solvent may be increased to 60 to 80%, then for 5 to 20 minutes the ratio of the second solvent slowly increased to 81 to 94%, then for 0.1 to 5 minutes the ratio of the second solvent increased to 95 to 99%, and then for 10 to 30 minutes the ratio of the second solvent maintained in 95 to 99%. However, the details of the gradient elution method can be determined experimentally and differently depending on the nature of the lipid to be analyzed.

Thus, when the ratio of the second solvent is adjusted to be higher by 95 to 99% in time using the gradient elution method in the separation step, the sample adsorbed in the lipid extraction device (10) may be detached to move into the analytical column (60) and to be separated depending on the hydrophobicity degree of the lipid in the analytical column (60). If the filler filled in the lipid extraction device (10) is HILIC and C4 and the filler of the analytical column (60) is C18, the hydrophobic lipid may flow out in the lipid extraction device (10) from the step that the composition of the second solvent is low to be again adsorbed at the end of the analytical column (60), and when the ratio of the second solvent is higher, it may be eluted in the analytical column (60), and then detected in the mass spectrometer (70).

The pretreatment step of the sample may comprise a step of mixing the sample and the alcohol and a step of taking the supernatant after centrifuging the mixture, and also comprise a sonication step to enhance the extraction efficiency. The reason for adding a certain amount of alcohol to the sample is for the purpose that proteins contained in the sample are coagulated or precipitated and at the same time the structural change of enzymes and the like present in the biological sample is caused to inhibit the activity, or the liquid molecules agglomerated from each other are dispersed to be well adsorbed on the filler. As the alcohol, methanol, ethanol and the like may be used. The mixing ratio of the sample and the alcohol may be, for example, 50 to 90% of the sample and 10 to 50% of the alcohol by a volume ratio. The mixing time can be from 1 to 10 min, for example. The centrifugation may be carried out, for example, at a speed of 1000 to 10000 g for 1 to 10 minutes, and the sonication step may be carried out for 3 to 10 minutes as a step prior to the centrifugation in order to improve the lipid extraction efficiency. In the present invention, the pretreatment of the sample is very simple as compared to the conventional liquid-liquid extraction method, since the lipid extraction device online connected to the system is used.

4. Beneficial Effects

The present invention is based on the liquid-solid extraction method, and may have a configuration that the capillary tubes (online lipid extraction device) filled with the filler having hydrophobic property are online connected among a high-performance liquid pump mounted with an autosampler, a liquid chromatography (analytical column), and a mass spectrometer using electrospray ionization method. In addition, by using two six port valves in the present invention, the sample is injected into the online extraction device, and the internal standard for quantification is injected directly into the analytical column (liquid chromatography) other than the online extraction device, so that the internal standard cannot be affected by the sample injection and impurity removal steps. Such an online extraction method has advantages that qualitative and quantitative analyses may be performed by only a small volume (several to tens μL) of a liquid biological sample, modification of the sample may be prevented by not exposing the sample to the air in the extraction procedure, and also the extraction procedure is very simple, so that various kinds of lipid samples may be simultaneously extracted within 10 minutes.

As described above, as the in vivo roles of lipids have been demonstrated one by one, this art is an actively growing trend, such as the term 'lipidomics' is commonly used. In one example, it is known that the coronary artery disease is very closely related to lipids, as it is a disease caused by accumulating lipoprotein particles with phospholipids and cholesterols in inner walls of blood vessels to cause a problem such as blood flow occlusion. The main components of low density lipoproteins or high density lipoproteins carrying these cholesterols are phospholipids and triacylglycerol, etc., the extensive research on lipids as their super ordinate concept may be essential for understanding the coronary artery disease, according to the recent study, the oxidized lipoproteins among the lipoproteins were pointed as a major cause narrowing the vessel walls by forming plaques on the inner walls of blood vessels when the number of the oxidized lipoproteins is too many, and the study on the oxidized phospholipids forming theses lipoproteins is also addressed as one of very important subjects.

In this case of such oxidized phospholipids, in vivo studies are significantly unsatisfactory, for which the reason may include points such that the oxidized lipids are difficult to be also easily analyzed by the mass spectrometer, since their kinds are very diverse and the amount is very small over general lipids, and the lipids are easily oxidized in contact with oxygen in the lipid extraction procedure, but it is finally expected to be capable of contributing to studies on the oxidized lipoproteins, since these problems may be overcome at once through the present invention.

In addition, the lipids have possibility that they may be utilized as a biomarker due to a close relation with in vivo signaling system, whereby a number of studies intended to use in diagnostic medicine are carried out. However, considering a practical problem that the amounts are restricted, which can draw blood and collect urine from patients, and these all cannot use in one or two inspections, it can be seen that the present invention has a great potential in the field of diagnostic medicine, in which hundreds of lipids can be used by just several to tens μL of a sample at the same time in detection and quantification.

Finally, it can be seen that the present invention has a very large value to be able to be utilized in the field of diagnostic medicine, in that no skill level is required, because the part that an experimenter directly involve about the sample is all to remove a supernatant through centrifugation after mixing the sample with an organic solvent such as methanol, and the time of taking online extraction is very short as a few minutes.

Example

1. Manufacturing of Online Lipid Extraction Device and Analytical Column

In the case of the online lipid extraction device, to a fused silica capillary tube (external diameter 365 μm, inner diameter 100 μm, manufactured by Polymicro Technologies, Phoenix, Ariz., USA), HILIC beads (particle average size 5 μm, trade name Nucleodur HILIC, manufactured by Macherey-nagel, Duren, Germany) as the first filler and C4 beads (pore size 100 Å, particle average size 5 μm, trade name Magic C4, manufactured by Bruker-Michrom manufacture, Auburn, Calif., USA) as the second filler were filled by each length of 2 cm to be a total of 4 cm. To charge the fillers, after connecting the inline filter (IDEX Health & Science manufacture, Oak Harbor, Wash.) only at one end of the capillary tube, the other end was immersed in a slurry made of C4 beads and the solvent (water 30% (v/v) and methanol 70% (v/v)) and pushed the helium gas in a pressure of 1000 psi to suck the filler up. After filling about 2 cm, the capillary tube was filled in the same way using the HILIC slurry and the other end of the capillary tube was also blocked by the inline filter. The average pore size of the porous plate mounted on the inline filter was about 0.5 μm.

In the case of the analytical column, after elongating one end of a fused silica capillary tube (external diameter 365 μm, inner diameter 100 μm, manufacture by Polymicro Technologies, Phoenix, Ariz., USA) to be about 10 μm as the needle tip, C18 beads (pore average size 100 Å, particle average size 3 μm, Watchers ODS-P C18 resin, manufactured by ISU Industry Co., Seoul, Korea) were filled thereto by about 7 cm in a pressure vessel as the above described method. The other end of the capillary tube was blocked by the inline filter to prevent from leaking filler.

2. Configuration of System for Extracting and Analyzing Lipids

As shown in FIG. 2, two six port valves, one lipid extraction device, one analytical column, sample injector, mass spectrometer, etc., were used, which were driven in a fully automatic using the two valves. One end of the first valve was configured by connecting the autosampler together with a high performance pump (HPLC) for the sample to be transferred, and containers of samples to be analyzed and an internal standard sample as the basis on quantitative analysis were mounted on the autosampler. As the mass spectrometer, TSQ vintage of Thermo Finnigan (San Jose, Calif., USA) was used, and as the LC, NanoAcquity UPLC of Waters (Milford, Mass., USA) equipped with an autosampler was connected and used. The first valve of FIG. 2 was a valve mounted within the UPLC, the second valve was a valve mounted on the mass spectrometer. As the first capillary tube to the tenth capillary tube, the fused silica capillary tubes (Polymicro Technologies, Phoenix, Ariz.) were used, the inner diameter of the tenth capillary tube was about 20 μm, and the inner diameter of the other capillary tubes was about 80 μm. The first joint (T joint) and the second joint (microcross) were used by purchasing them from IDEX Health & Science (Oak Harbor, Wash.). A Pt wire was connected to the second joint, to provide electric current to mass spectrometer.

3. Method for Extracting and Analyzing Lipids

All standard lipid materials were purchased from Avanti Polar Lipid, Inc. (Alabaster, Ala.), all HPLC grade solvents used for the LC were purchased from J. T. Baker (Phillipsburg, N.J.), modifiers, such as ammonium hydroxide and ammonium formate, mixed together with the solvent were purchased from Sigma-Aldrich Co. (St. Louis, Mo.).

Solvents were used in two types, including a polar solvent mostly consisted of water, and an organic solvent. The first solvent (solvent A) was composed of 90% (v/v) water and 10% (v/v) acetonitrile, and the second solvent (solvent B) was composed of 20% (v/v) acetonitrile, 20% (v/v) methanol, and 60% (v/v) isopropanol. 10 mM of ammonium formate and 0.05% of ammonium hydroxide were added to each solvent. Samples were injected when 100% of the first solvent flowed, and the ratio of the second solvent was gradually increased, as the analysis (separation step) started. Specifically, the ratio of the second solvent was increased to 70% for 0.5 minutes, after that, slowly increased to 90% for 10 minutes, after that, raised for 1 minute to 97%, and then maintained at 97% for 20 minutes.

Extraction and analysis of the sample was composed of three steps in total, and the two valves at each step were set up through organic movement so as to be capable of controlling flow of the fluid.

First, by setting the two valves all in (A, A) mode, the biological sample to be analyzed was injected via the autosampler into the online lipid extraction device. At this time, the fluid used was 100% of the polar solvent (first solvent), and this solvent passed through the lipid extraction device, and flowed out to the eighth capillary tube of the second valve, without being discharged towards the analytical column in the microcross connected by the Pt wire. After the sample was adsorbed on the online lipid extraction device, the hydrophilic peptides and low molecular materials and inorganic ions, present in the sample, were removed by draining the polar solvent for 5 minutes.

Next, by adjusting the valves to be set in (B, B) mode, the fluid flowed out of the autosampler was allowed to flow 100% into only the analytical column. At this time, by injecting the internal standard it was allowed to be adsorbed directly in the inlet of the analytical column.

Finally, the valves were set in (A, B) mode. The solvent was divided in the inlet of the lipid extraction device to move, that is, some (about 10%) of the solvent passed through the lipid extraction device and the analytical column in turn, and then flowed to the inlet of the mass spectrometer, and the remaining solvent (about 90%) flowed into the tenth capillary tube. At this time, although the solvent flowed out of the autosampler was a unit of from several to tens μLμL/min, the solvent was allowed to flow by 300 to 1000 nL/min into a direction of the analytical column and the mass spectrometer. Also, in this step the ratio of the second solvent was controlled using the gradient elution method to be increased to 97% over time.

Test Example

1. Internal Standard Test

Figure 3:
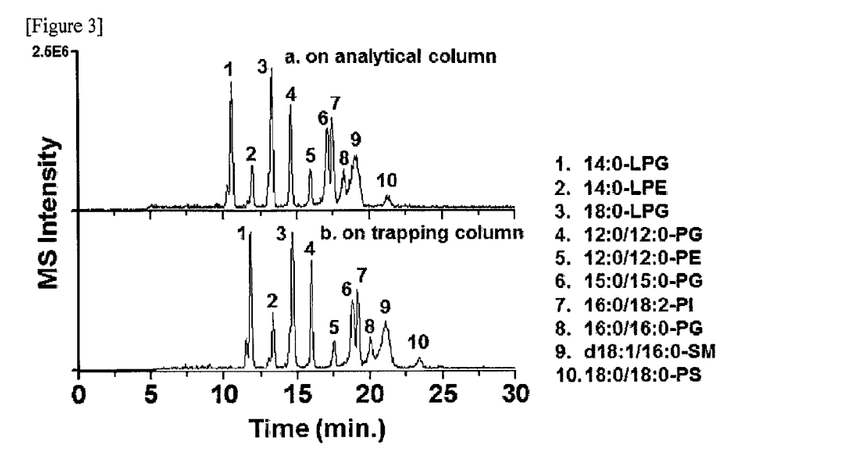
FIG. 3 shows the results of tests using the standard lipid material according to the present invention.

FIG. 3 is a chromatogram detecting 10 lipid internal standards using the apparatus of the present invention, wherein a is one directly injected into the analytical column, and b is one adsorbed by internal standards on the lipid extraction device. Lipid internal standards were tested by injecting them twice by each 3 pmol, with recording kinds of internal standards on the right side of FIG. 3. a in FIG. 3 is one directly injected into the analytical column by setting the valves in (B, B) mode, and b in FIG. 3 is one analyzed after injecting internal standards into the lipid extraction device by setting the valves in (A, A) mode. All the valves were set in (A, B) mode on separation and detection.

In FIG. 3 it can be seen that the overall retention time in a is slightly faster than one in b, which is found because it takes additional time to pass through the section connecting between the lipid extraction device and the analytical column. In light of the fact that the resolutions between peaks of two chromatograms are not much different, it can be seen that the resolution reduction by diffusion phenomenon of the sample does not occur during passing through the dead volume of the section connecting between the lipid extraction device and the analytical column. Also, it can be seen that the height of peaks is not much different as well, and it is possible from this fact to confirm at a rough estimate the fact that the sample is also significantly well adsorbed on the lipid extraction device. This result is to address once again in FIG. 4 below. The peaks of numbers 1 to 3 showing lysophospholipids are represented as a shoulder peak form, since two structural isomers are not fully separated due to the property that two structural isomers are present.

2. Comparison of Lipid Extraction Efficiency

Figure 4:
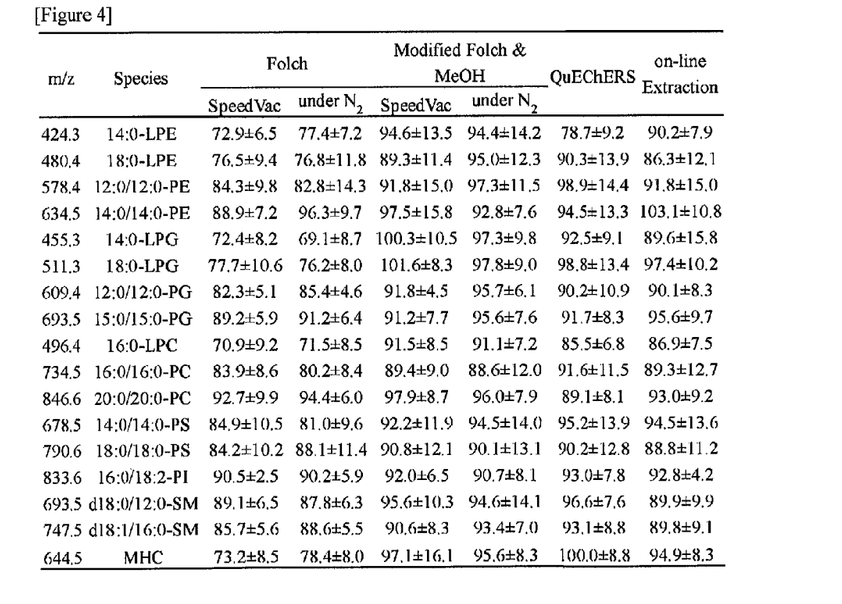
FIG. 4 shows the results of comparing the lipid extraction efficiency of the present invention and the conventional extraction method.

FIG. 4 is a comparison of lipid extraction efficiency of the extraction method of the present invention and a variety of existing lipid extraction methods. An internal standard was mixed with a urine sample, extracted by each extraction method, dissolved in the first solvent (solvent A), and detected by the mass spectrometer to calculate the peak area, but the relative amounts were compared after allowing the amount of the internal standard directly injected into the mass spectrometer to be 100. In FIG. 4, 'm/z' is supposed to be a mass as mass/charge, and 'SpeedVac' and 'under $N_2$' are those that classify the evaporation method of the liquid solvent, that is, 'SpeedVac' is the case of evaporation by a vacuum, and 'under $N_2$' is the case of using nitrogen for oxidation inhibition.

To compare the Folch method to be conventionally widely used, the modified Folch & MeOH method being modified in the laboratory of the inventors, the QuCHERS method, and the like with the online extraction method set forth in the present invention for each other, the internal standard was mixed with the urine sample to be 500 fmol/μL and the amount of the internal standard was measured after completing extraction. The sample as the basis is one obtained by mixing the internal standard with the first solvent to be the same concentration and then performing no extraction procedure, and set the peak area detected after being directly injected into the mass spectrometer set as 100. To correct each of the ionization efficiency, the relative quantification values represented after separately injecting 3 pmol of 15:0/15:0-PG into the analytical column were used in all the detected peaks. The analytical sample, which uses the sample mixing the urine sample and water in a volume ratio of 5:3, was used in the other extraction methods except for the online extraction method according to the present invention.

First, in the case of the Folch method, the separated supernatant was recovered by mixing 40 μL of methanol and 100 μL of chloroform with 200 μL of samples for 30 minutes and then centrifuging (5000 g, 10 min) the mixture, and dried with SpeedVac, and the same sample was prepared by the same way, and then dried in an appliance that nitrogen gas was flowing.

In the case of the modified Folch & MeOH extraction method, the under layer was separated by mixing 200 μL of the sample with 40 μL of methanol and 100 μL of MTBE for 30 minutes, and then centrifuging the mixture in the conditions as above. Then, after adding 100 μL of methanol to the supernatant, followed by one again mixing and centrifugation, only the supernatant was separated, mixed with the previous under layer, and then dried with SpeedVac. The same sample was pretreated by the same way, but dried in the appliance that nitrogen gas was flowing. The prepared four samples were diluted with 20 μL of chloroform, 80 μL of an organic solvent (acetonitrile:methanol=1:9, v/v), and 100 μL of the first solvent and prepared to be a total of 200 μL.

In the case of the QuEChERS extraction method, first the supernatant was recovered by mixing 200 μL of the urine sample with 300 mg of the extraction kit ($MgSO_4$:$CH_3COONa$=5:1, m/m) and 400 μL of the mixed solution (chloroform:methanol=2:1, v/v) for 1 minute and then centrifuging the mixture at 10000 g for 10 minutes, and after once again mixing it with 50 mg of C18 beads, followed by centrifugation, only the supernatant was separated and diluted with the first solvent to be a final volume of 200 μL.

Finally, in the case of the online extraction method of the present invention, the supernatant was separated by mixing 125 μL of the urine sample and 75 μL of methanol for 5 minutes and then centrifuging the mixture at 5000 g for 5 minutes as the pretreatment of the sample.

All the prepared samples were injected into the mass spectrometer by 20 μL. The other extraction samples except for the extraction method of the present invention were detected by injecting them in a state that the valves were set in (B, B) mode and changing the valves to (A, B) mode after once again injecting 3 pmol of 15:0/15:0-PG. In the case of the online extraction method of the present invention the sample was detected by injecting it in (A, A) mode and changing the valves to (A, B) mode after injecting 15:0/15:0-PG in (B, B) mode.

Referring to FIG. 4, since the extraction efficiency of the Folch method in the lysophospholipid parts is about 70 to 80%, it can be seen that the efficiency is low as compared to other extraction methods. This is a reason to develop the modified Folch & MeOH method in the laboratory of the present inventors, which shows a trend similar to the first published literature (S. K. Byeon, J. Y. Lee, M. H. Moon Analyst 137 (2012) 451). In addition, since the Folch method mostly shows the extraction efficiency of 80%, even in the case of the other lipids, it can be seen that it exhibits a low yield over the recently developed liquid-liquid extraction method as a whole. On the other hand, the modified Folch & MeOH and QuCHERS extraction methods exhibit a high yield of 90% or so about almost the whole lipids, and considering that the final drying time is usually about 10 hours in the procedure of preparing the sample, it can be seen that the QuCHERS method exhibits a high yield in a level similar to the modified Folch & MeOH method, despite having very short time in preparing the sample. Finally, the results of the online extraction method of the present invention are similar as a whole as compared with the two extraction methods above, and it can be seen that there is no significant difference within 5% error range. Considering the preparation time, it represents no great difference in a slightly shorter level than the QuCHERS method, but since the QuCHERS method requires significantly proficient skills in the sample pretreatment procedure, it is determined that the present invention has a great advantage in that most extraction procedures are automated.

DESCRIPTION OF REFERENCES

10: lipid extraction device
11: capillary tube
12: first filler
13: second filler
14: filter
15: porous plate
20: sample injector
30: first capillary tube
31: second capillary tube
32: third capillary tube
33: fourth capillary tube
34: fifth capillary tube
35: sixth capillary tube
36: seventh capillary tube
37: eighth capillary tube
38: ninth capillary tube
39: tenth capillary tube
40: first valve
50: first joint
51: second joint
60: analytical column
70: mass spectrometer
71: wire
80: second valve

The invention claimed is:

1. A system for extracting and analyzing lipids comprising
a sample injector;
a first valve connected with the sample injector via a first capillary tube;
a first joint connected with the first valve via a second capillary tube;
a lipid extracting device having the inlet side connected with the first joint via a third capillary tube and the outlet side connected with the first valve via a fourth capillary tube;
a second joint connected with the first valve via a fifth capillary tube;
an analytical column connected with the second joint via a sixth capillary tube;
a mass spectrometer connected with the analytical column; and
a second valve connected with the second joint via a seventh capillary tube, connected with an eighth capillary tube, connected with the first joint via a ninth capillary tube and connected with a tenth capillary tube,
wherein the lipid extraction device comprises a capillary tube,
wherein the capillary tube of the lipid extraction device comprises a first region containing a first filler; and a second region present in a region other than the first region and containing a second filler having polarity different from the first filler.

2. The system for extracting and analyzing lipids according to claim 1, further comprising a filter that is installed on both ends of the capillary tube of the lipid extraction device.

3. The system for extracting and analyzing lipids according to claim 1, wherein the first filler is hydrophilic interaction liquid chromatography beads (HILIC).

4. The system for extracting and analyzing lipids according to claim 1, wherein the second filler is at least one selected from the group consisting of C4 beads containing butyl chains, C8 beads containing octyl chains, and C18 beads containing octadecyl chains.

5. The system for extracting and analyzing lipids according to claim 1, further comprising a porous plate installed on both ends of the capillary tube of the lipid extraction device and comprising pores having an average size of 0.1 to 1.5 μm.

6. The system for extracting and analyzing lipids according to claim 1, wherein the sample injector is an autosampler, which is mounted on high-performance liquid chromatography (HPLC).

7. The system for extracting and analyzing lipids according to claim 1, wherein
the first valve is a six port valve comprising a first port to a sixth port, which is mounted on the high-performance liquid chromatography (HPLC), and
the first port of the first valve is connected with the first capillary tube,
the second port of the first valve is connected with the second capillary tube,
the third port of the first valve is connected with the fourth capillary tube, and
the fourth port of the first valve is connected with the fifth capillary tube.

8. The system for extracting and analyzing lipids according to claim 1, wherein
the second valve is the six port valve comprising the first port to the sixth port, which is mounted on the mass spectrometer, and
the first port of the second valve is connected with the seventh capillary tube,
the second port of the second valve is connected with the eighth capillary tube,
the third port of the second valve is connected with the ninth capillary tube, and
the fourth port of the second valve is connected with the tenth capillary tube.

9. The system for extracting and analyzing lipids according to claim 1, wherein the inner diameter of the first capillary tube to the ninth capillary tube is 50 to 100 μm, and the inner diameter of the tenth capillary tube is 5 to 40 μm.

10. The system for extracting and analyzing lipids according to claim 1, wherein the first joint is a T joint, and the second joint is a cross joint, and wherein a wire connected with an electrode of the mass spectrometer is installed on the second joint.

11. The system for extracting and analyzing lipids according to claim 1, wherein the analytical column comprises C18 beads containing octadecyl chains, which has a taper structure at the end.

12. A method for extracting and analyzing lipids which uses the system for extracting and analyzing lipids of claim 1, and comprises a sample injection step, an internal standard injection step and a separation step.

13. The method for extracting and analyzing lipids according to claim 12, wherein
the first valve is a six port valve comprising a first port to a sixth port, which is mounted on the high-performance liquid chromatography (HPLC), and the first port of the first valve is connected with the first capillary tube, the second port of the first valve is connected with the second capillary tube, the third port of the first valve is connected with the fourth capillary tube, and the fourth port of the first valve is connected with the fifth capillary tube, the second valve is the six port valve comprising the first port to the sixth port, which is mounted on the mass spectrometer, and the first port of the second valve is connected with the seventh capillary tube, the second port of the second valve is connected with the eighth capillary tube, the third port of the second valve is connected with the ninth capillary tube, and the fourth port of the second valve is connected with the tenth capillary tube.

14. The method for extracting and analyzing lipids according to claim 13, wherein in the sample injection step a fluid is introduced through the sample injector and then moved into the eighth capillary tube, via the first capillary tube, the first port and the second port of the first valve, the second capillary tube, the first joint, the third capillary tube, the lipid extraction device, the fourth capillary tube, the third port and the fourth port of the first valve, the fifth capillary tube, the second joint, the seventh capillary tube, and the first port and the second port of the second valve.

15. The method for extracting and analyzing lipids according to claim 13, wherein in the internal standard injection step a fluid is introduced through the sample injector and then moved into the analytical column, via the first capillary tube, the first port and the fourth port of the first valve, the fifth capillary tube, the second joint, and the sixth capillary tube.

16. The method for extracting and analyzing lipids according to claim 13, wherein in the separation step a fluid is introduced through the sample injector and then moved into the first joint via the first capillary tube, the first port and the second port of the first valve and the second capillary tube, and some of the fluid in the first joint is moved into the analytical column via the third capillary tube, the lipid extraction device, the fourth capillary tube, the third port and the fourth port of the first valve, the fifth capillary tube, the second joint and the sixth capillary tube, and the remaining fluid in the first joint is moved into the tenth capillary tube via the ninth capillary tube, and the third port and the fourth port of the second valve.

* * * * *